US009382547B2

(12) United States Patent
Goldman et al.

(10) Patent No.: US 9,382,547 B2
(45) Date of Patent: Jul. 5, 2016

(54) **HUMAN OPTIMIZED *BACILLUS ANTHRACIS* PROTECTIVE ANTIGEN**

(71) Applicants: Stanley Goldman, Walnut Creek, CA (US); Mark Albrecht, Washington, DC (US)

(72) Inventors: Stanley Goldman, Walnut Creek, CA (US); Mark Albrecht, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/190,464

(22) Filed: Feb. 26, 2014

(65) Prior Publication Data

US 2015/0240245 A1    Aug. 27, 2015

(51) Int. Cl.
| | |
|---|---|
| *C12N 15/64* | (2006.01) |
| *A61K 39/07* | (2006.01) |
| *C07K 14/32* | (2006.01) |
| *A61K 39/00* | (2006.01) |

(52) U.S. Cl.
CPC .............. *C12N 15/64* (2013.01); *A61K 39/07* (2013.01); *C07K 14/32* (2013.01); *A61K 2039/53* (2013.01); *A61K 2039/55511* (2013.01)

(58) Field of Classification Search
None
See application file for complete search history.

(56) References Cited

U.S. PATENT DOCUMENTS

| | | | | |
|---|---|---|---|---|
| 5,591,631 | A  * | 1/1997 | Leppla et al. | 435/252.3 |
| 5,677,274 | A  * | 10/1997 | Leppla et al. | 514/7.6 |
| 6,770,479 | B1 * | 8/2004 | Lee et al. | 435/456 |
| 7,037,503 | B2 * | 5/2006 | Collier et al. | 424/190.1 |
| 7,201,912 | B2 * | 4/2007 | Park et al. | 424/246.1 |
| 7,358,334 | B1 * | 4/2008 | Chaplin | 530/350 |
| 7,638,333 | B2 * | 12/2009 | Lee et al. | 435/456 |
| 7,763,451 | B2 * | 7/2010 | Shiloach et al. | 435/243 |
| 8,044,189 | B2 * | 10/2011 | Leppla et al. | 536/23.7 |
| 8,101,735 | B2 * | 1/2012 | Brehm et al. | 536/23.1 |
| 8,313,928 | B2 * | 11/2012 | Williamson et al. | 435/69.3 |
| 8,323,927 | B2 * | 12/2012 | Brehra et al. | 435/69.3 |
| 8,394,387 | B1 * | 3/2013 | Leppla et al. | 424/246.1 |
| 8,440,247 | B2 * | 5/2013 | Lee et al. | 426/597 |
| 8,569,015 | B2 * | 10/2013 | Rasochova et al. | 435/69.1 |
| 8,703,150 | B2 * | 4/2014 | Leppla et al. | 424/246.1 |
| 8,728,760 | B2 * | 5/2014 | Galen et al. | 435/69.1 |
| 8,754,015 | B2 * | 6/2014 | Dewhurst et al. | 506/26 |
| 2010/0272757 | A1 * | 10/2010 | Leppla et al. | 424/246.1 |
| 2011/0110968 | A1 * | 5/2011 | Goldman et al. | 424/190.1 |
| 2015/0017127 | A1 * | 1/2015 | O'Shea et al. | 424/93.2 |
| 2015/0044210 | A1 * | 2/2015 | Mechaly et al. | 424/134.1 |

FOREIGN PATENT DOCUMENTS

WO     WO 2008/027099     *   3/2008

* cited by examiner

*Primary Examiner* — Nita M Minnifield
(74) *Attorney, Agent, or Firm* — Albert M. Churilla; Ning Yang; Diane P. Tso

(57) ABSTRACT

The invention relates to a humanized nucleic acid construct from *Bacillus anthracis* protective antigen (PA) gene and method of modifying the gene. The humanized gene, and method of producing it, improves the structural fidelity of expressed protein product, when produced in mammalian host cells, to native, bacterially produced protein. The construct is useful in nucleic acid based vaccine formulations against *B. anthracis*.

5 Claims, 8 Drawing Sheets

```
HoPA    GAAGTGAAGCAGGAGAATCGGCTGCTGAATGAATCCGAGAGCAGCTCTCAGGGCTTGCTG 60
Wt-PA   GAAGTTAAACAGGAGAACCGGTTATTAAATGAATCAGAATCAAGTTCCCAGGGGTTACTA 60
        ***** ** ******** *** *  * ******** **    ** ** ***** ** **

HoPA    GGGTATTACTTCTCTGACCTGAATTTCCAGGCACCCATGGTCGTCACATCCTCTACCACC 120
Wt-PA   GGATACTATTTTAGTGATTTGAATTTTCAAGCACCCATGGTGGTTACCTCTTCTACTACA 120
        ** ** ** **   ***  ******* ** *********** ** ** ** ***** **

HoPA    GGAGACCTATCGATTCCCTCAAGCGAGCTGGAGAATATCCCTTCAGAGAACCAGTATTTT 180
Wt-PA   GGGGATTTATCTATTCCTAGTTCTGAGTTAGAAAATATTCCATCGGAAAACCAATATTTT 180
        ** **  **** *****       *** * ** ***** ** ** ** ***** ******

HoPA    CAATCCGCAATCTGGTCCGGCTTCATTAAAGTGAAGAAGTCTGATGAATACACCTTCGCC 240
Wt-PA   CAATCTGCTATTTGGTCAGGATTTATCAAAGTTAAGAAGAGTGATGAATATACATTTGCT 240
        ***** ** ** ***** ** ** ** ***** ******  ********* ** ** **

HoPA    ACTTCCGCAGACAATCACGTTACCATGTGGGTGGACGACCAAGAAGTCATTAATAAAGCC 300
wt-PA   ACTTCCGCTGATAATCATGTAACAATGTGGGTAGATGACCAAGAAGTGATTAATAAAGCT 300
        ******** ** ***** ** ** ******** ** *********** ***********

HoPA    TCTAATTCCAATAAAATCAGACTCGAAAAGGGCAGACTTTATCAGATCAAGATTCAGTAC 360
wt-PA   TCTAATTCTAACAAAATCAGATTAGAAAAAGGAAGATTATATCAAATAAAAATTCAATAT 360
        ******** ** ********* * ***** ** *** * ***** ** ** ***** **

HoPA    CAGAGGGAGAATCCCACAGAAAAAGGTTTGGATTTCAAATTGTATTGGACAGATAGTCAG 420
wt-PA   CAACGAGAAAATCCTACTGAAAAAGGATTGGATTTCAAGTTGTACTGGACCGATTCTCAA 420
        **  * ** ***** ** ******** *********** ***** ***** ***  ***

HoPA    AATAAGAAAGAGGTGATATCCTCTGACAACCTCCAGCTGCCCGAATTGAAACAAAAATCA 480
wt-PA   AATAAAAAAGAAGTGATTTCTAGTGATAACTTACAATTGCCAGAATTAAAACAAAAATCT 480
        ***** ***** ***** **   *** *** * **  **** ***** ***********

HoPA    TCAAATTCACGGAAGAAGCGCTCTACCTCAGCCGGCCCAACCGTCCCTGACAGAGATAAC 540
wt-PA   TCGAACTCAAGAAAAAAGCGAAGTACAAGTGCTGGACCTACGGTTCCAGACCGTGACAAT 540
        ** ** *** * ** *****   ***    ** ** ** ** ** ** *** * ** **

HoPA    GACGGGATTCCAGATTCTCTGGAGGTTGAGGGCTACACAGTGGACGTAAAGAACAAGAGA 600
wt-PA   GATGGAATCCCTGATTCATTAGAGGTAGAAGGATATACGGTTGATGTCAAAAATAAAAGA 600
        ** ** ** ** *****  * ***** ** ** ** ** ** ** ** ** ** ** ***

HoPA    ACCTTTTTGAGTCCTTGGATTTCAAACATTCATGAGAAGAAGGGACTTACTAAGTACAAG 660
wt-PA   ACTTTTCTTTCACCATGGATTTCTAATATTCATGAAAAGAAAGGATTAACCAAATATAAA 660
        ** *** *    ** ******** ** ******** ***** *** * ** ** ** **

HoPA    TCTAGCCCAGAGAAATGGAGCACAGCCTCCGATCCATACTCGGACTTCGAGAAGGTCACC 720
wt-PA   TCATCTCCTGAAAAATGGAGCACGGCTTCTGATCCGTACAGTGATTTCGAAAAGGTTACA 720
        **    ** ** *********** ** ** ***** ***   ** ***** ***** **

HoPA    GGACGCATCGATAAGAATGTAAGCCCAGAGGCTCGGCATCCACTGGTGGCTGCCTATCCC 780
wt-PA   GGACGGATTGATAAGAATGTATCACCAGAGGCAAGACACCCCCTTGTGGCAGCTTATCCG 780
        ***** ** ************   ******** * ** ** ** ***** ** *****
```

FIG. 1A

```
HoPA    ATTGTGCACGTGGATATGGAAAATATTATTCTCAGCAAGAACGAGGATCAGTCCACTCAA 840
wt-PA   ATTGTACATGTAGATATGGAGAATATTATTCTCTCAAAAAATGAGGATCAATCCACACAG 840
        ***** ** ** ******** ************   ** ** ******** ***** **

HoPA    ACACGGACTCCGAGACAAGAACCATCAGCAAGAACACATCTACAAGTAGAACTCATACA 900
wt-PA   AATACTGATAGTGAAACGAGAACAATAAGTAAAAATACTTCTACAAGTAGGACACATACT 900
        ** ** **    ** ** ***** ** ** ** ** ** *********** ** *****

HoPA    TCAGAGGTGCACGGCAACGCCGAGGTTCACGCCAGTTTCTTCGATATCGGGGGCAGTGTT 960
wt-PA   AGTGAAGTACATGGAAATGCAGAAGTGCATGCGTCGTTCTTTGATATTGGTGGGAGTGTA 960
        ** ** ** ** ** ** ** ** ** **    ***** ***** ** ** *****

HoPA    AGCGCCGGATTTTCTAACTCCAACAGCTCTACAGTGGCTATCGACCACTCTCTGAGTCTC 1020
wt-PA   TCTGCAGGATTTAGTAATTCGAATTCAAGTACGGTCGCAATTGATCATTCACTATCTCTA 1020
        ** ******  *** ** **      *** ** ** ** ** ** ** **   ***

HoPA    GCAGGGGAGCGGACGTGGGCGGAAACCATGGGCCTGAACACCGCCGATACAGCCAGGTTG 1080
wt-PA   GCAGGGGAAAGAACTTGGGCTGAAACAATGGGTTTAAATACCGCTGATACAGCAAGATTA 1080
        ********  * ** ***** ***** *****  * ** ***** ******** ** **

HoPA    AATGCAAACATTCGCTATGTGAATACAGGTACCGCTCCCATCTATAATGTCCTTCCTACT 1140
wt-PA   AATGCCAATATTAGATATGTAAATACTGGGACGGCTCCAATCTACAACGTGTTACCAACG 1140
        ***** ** *** * ***** ***** ** ** ***** ***** ** **  * ** **

HoPA    ACATCTCTCGTGTTGGGGAAAAATCAGACCCTGGCAACAATCAAGGCCAAGGAGAATCAG 1200
wt-PA   ACTTCGTTAGTGTTAGGAAAAAATCAAACACTCGCGACAATTAAAGCTAAGGAAAACCAA 1200
        ** **  * ***** ** ******** ** ** ** ***** ** ** ***** ** **

HoPA    CTGAGTCAGATACTCGCACCCAATAACTACTACCCATCAAAGAATCTTGCACCTATAGCT 1260
wt-PA   TTAAGTCAAATACTTGCACCTAATAATTATTATCCTTCTAAAAACTTGGCGCCAATCGCA 1260
         * ***** ***** ***** ***** ** ** ** ** ** **  * ** ** ** **

HoPA    CTGAACGCCCAGGATGATTTTAGCAGCACCCCAATTACTATGAATTATAACCAGTTCCTG 1320
wt-PA   TTAAATGCACAAGACGATTTCAGTTCTACTCCAATTACAATGAATTACAATCAATTTCTT 1320
         * ** ** ** ***** **    ** ******** ******** ** ** ** **

HoPA    GAGTTGGAGAAGACTAAGCAATTGAGGCTGGATACAGACCAAGTGTACGGCAATATAGCT 1380
wt-PA   GAGTTAGAAAAAACGAAACAATTAAGATTAGATACGGATCAAGTATATGGGAATATAGCA 1380
        ***** ** ** ** ** ***** **  * ***** ** ***** ** ** ********

HoPA    ACTTATAACTTCGAGAATGGGAGGGTTAGGGTGGACACAGGGAGCAATTGGTCGGAAGTG 1440
wt-PA   ACATACAATTTTGAAAATGGAAGAGTGAGGGTGGATACAGGCTCGAACTGGAGTGAAGTG 1440
        ** ** ** ** ** ***** ** ** ******** *****    ** ***   ******

HoPA    CTTCCACAAATTCAGGAGACCACAGCCAGAATCATCTTTAATGGCAAGGACCTCAACCTT 1500
wt-PA   TTACCGCAAATTCAAGAAACAACTGCACGTATCATTTTTAATGGAAAAGATTTAAATCTG 1500
         * ** ******** ** ** ** **  * ***** ******** ** **  * ** **

HoPA    GTGGAAAGGAGAATTGCCGCAGTTAACCCAAGTGACCCCTTGGAAACAACCAAGCCAGAC 1560
wt-PA   GTAGAAAGGCGGATAGCGGCGGTTAATCCTAGTGATCCATTAGAAACGACTAAACCGGAT 1560
        ** ****** * ** ** ** ***** ** ***** ** ** ***** ** ** ** **
```

FIG. 1B

```
HoPA    ATGACTCTGAAGGAAGCCCTGAAGATCGCTTTCGGGTTTAATGAACCAAACGGCAACCTG 1620
wt-PA   ATGACATTAAAAGAAGCCCTTAAAATAGCATTTGGATTTAACGAACCGAATGGAAACTTA 1620
        *****  * ** ******** ** ** ** ** ** ***** ***** ** ** *** *

HoPA    CAGTACCAGGGAAAGGACATTACCGAGTTTGACTTTAATTTCGATCAGCAGACCTCCCAA 1680
wt-PA   CAATATCAAGGGAAAGACATAACCGAATTTGATTTTAATTTCGATCAACAAACATCTCAA 1680
        ** ** ** ** ** ***** ***** ***** ************** ** ** ** ***

HoPA    AACATCAAGAATCAACTGGCCGAGCTGAACGCTACAAATATTTATACCGTGCTCGACAAG 1740
wt-PA   AATATCAAGAATCAGTTAGCGGAATTAAACGCAACTAACATATATACTGTATTAGATAAA 1740
        ** ***********  * ** **  * ***** ** ** ** ***** **  * ** **

HoPA    ATTAAATTGAACGCGAAGATGAATATCTTGATACGCGATAAGCGCTTTCATTACGACCGC 1800
wt-PA   ATCAAATTAAATGCAAAAATGAATATTTTAATAAGAGATAAACGTTTTCATTATGATAGA 1800
        ** ***** ** ** ** ******** ** *** * ***** ** ******** **  *

HoPA    AACAATATAGCCGTTGGCGCCGACGAATCTGTCGTAAAAGAGGCCCACAGAGAAGTGATT 1860
wt-PA   AATAACATAGCAGTTGGGGCGGATGAGTCAGTAGTTAAGGAGGCTCATAGAGAAGTAATT 1860
        ** ** ***** ***** ** ** ** ** ** ** ** ***** ** ******** ***

HoPA    AACTCCAGCACCGAAGGGCTCCTGCTGAACATTGATAAAGACATCCGCAAGATCCTGTCC 1920
wt-PA   AATTCGTCAACAGAGGGATTATTGTTAAATATTGATAAGGATATAAGAAAAATATTATCA 1920
        ** **    ** ** **  *  ** * ** ******** ** **  * ** **  * **

HoPA    GGGTACATAGTGGAGATCGAGGACACCGAGGGACTCAAAGAAGTAATCAACGACCGGTAC 1980
wt-PA   GGTTATATTGTAGAAATTGAAGATACTGAAGGGCTTAAAGAAGTTATAAATGACAGATAT 1980
        ** ** ** ** ** ** ** ** ** ** ** ** ******** ** ** *** * **

HoPA    GATATGCTGAATATCTCAAGCCTCCGGCAAGACGGGAAGACTTTCATAGATTTCAAGAAA 2040
wt-PA   GATATGTTGAATATTTCTAGTTTACGGCAAGATGGAAAAACATTTATAGATTTTAAAAAA 2040
        ****** ******* ** **  * ******** ** ** ** ** ******** ** ***

HoPA    TACAACGACAAGCTGCCACTCTATATCTCAAACCCCAATTACAAGGTGAACGTTTACGCA 2100
wt-PA   TATAATGATAAATTACCGTTATATATAAGTAATCCCAATTATAAGGTAAATGTATATGCT 2100
        ** ** ** **  * **  * *****    ** ******** ***** ** ** ** **

HoPA    GTCACCAAAGAGAACACCATCATTAATCCATCAGAAAATGGTGACACAAGTACTAATGGT 2160
wt-PA   GTTACTAAAGAAAACACTATTATTAATCCTAGTGAGAATGGGGATACTAGTACCAACGGG 2160
        ** ** ***** ***** ** ********    ** ***** ** ** ***** ** **

HoPA    ATTAAGAAGATTCTCATTTTCAGCAAGAAGGGGTATGAGATCGGCTAA 2208
wt-PA   ATCAAGAAAATTTTAATCTTTTCTAAAAAAGGCTATGAGATAGGATAA 2208
        ** ***** *** * ** **    ** ** ** ******** ** ***
```

HUMAN OPTIMIZED BACILLUS ANTHRACIS PROTECTIVE ANTIGEN

CROSS-REFERENCES TO RELATED APPLICATIONS

This application is a Divisional Application of U.S. application Ser. No. 12/916,889, filed 1 Nov. 2010, which claims the benefit of U.S. Provisional Application No. 61/260,656, filed 12 Nov. 2009, which are incorporated herein by reference.

BACKGROUND OF INVENTION

1. Field of Invention

The inventive subject matter relates to a codon optimized nucleic acid sequence of Bacillus anthracis protective antigen (PA). The method of codon optimization of the gene is aimed at improving expression in mammals, including humans, as well as enhancing immunogenicity against endogenously produced PA protein. The inventive construct, incorporated into DNA expression systems, can be useful as a component of immunogenic compositions against B. anthracis, such as vaccines.

2. Background Art

B. anthracis, the etiological agent of anthrax, is a spore-forming, gram positive bacterium. Infection can occur through a variety of routes including cutaneous and gastrointestinal, however, inhalational anthrax is the most widely recognized and feared (Baillie, J. Appl Microbiol., 91: 609-613 (2001)). Following inhalation, the majority of the aerosolized spores are immediately phagocytized by alveolar macrophages and transported through the lymphatic channels to hilar and tracheobronchial lymph nodes. This rapidly leads to the multiplication and systemic circulation of vegetative bacilli. It is believed that en route to these regional lymph nodes the spores begin to germinate and multiply within the macrophage.

Advanced stages of infection are predicated on B. anthracis' anti-phagocytic capsule and the secretion of a tripartite exotoxin consisting of a cell binding component, Protective Antigen (PA), which binds to two enzymatically active subunits: Lethal Factor (LF) or Edema Factor (EF) to form lethal toxin (LeTx) and edema toxin (EdTx), respectively. The currently available licensed human vaccine for B. anthracis (BioThrax) is a filtered extract from B. anthracis absorbed to alum and is primarily composed of PA.

SUMMARY OF THE INVENTION

An object of the invention is a humanized, i.e., codon optimized, DNA construct of Bacillus anthracis protective antigen. The modifications enable efficient translation of PA in mammals, including humans.

Another object of the invention is a method of codon optimization utilizing rare host codons in place of rare bacterial codons, rather than those most highly utilized by the host. This enables ribosomal stalling at appropriate places along the gene to ensure intra-molecular associations occur within the nascent protein similar to that which would occur naturally. Correct folding of PA would result in a more efficacious immune response against naturally occurring B. anthracis expressed PA.

A further object of the invention is a method of human optimization whereby codon optimization does not consist of replacing all bacterial codons throughout the length of the gene with the most highly or frequently used codons in the host cell. Instead, the inventive method utilizes consideration of a number of factors in order to afford increased expression efficiency in a mammalian (e.g., human) host cell, as well as an yielding an expressed protein similar in structure to the native, B. anthracis, PA protein.

The first factor considered is protein expression efficiency. By incorporating codons that are highly utilized in the mammalian host cell for the first 50 codons of the bacterial sequence, the mammalian ribosome will effectively engage the mRNA, decreasing the likelihood of early termination of the ribosome is minimized. Another factor is to maximize the opportunity for correct protein folding. This is afforded by first searching for regions in the native PA sequence where rare codons are utilized in the bacterial gene. Regions were rare codons are heavily utilized may result in, normal, native PA expression, specifically proper folding of the expressed protein. In the modified sequence, these use of rare codons is maintained by substituting rare codons from the human bias table. This would permit the ribosome to stall, where it normally would when expressing native PA in the bacteria, and permit normal folding to occur. Another factor is to ensure against unwarranted deletions of mRNA. Therefore, the bacterial sequence is analyzed to search for ribosomal splice sites to ensure that post-transcriptional machinery of mammalian cells did not delete sections of the mRNA. Finally, an analysis of the bacterial sequence is undertaken to identify any regions of complementarity. These regions are important since they could potentially result in the single stranded RNA folding back on itself resulting in unwanted host cell operations, such as ribosomal stalling or premature termination of translation.

BRIEF DESCRIPTION OF DRAWINGS

FIG. 1(A-C). Alignment of the human optimized sequence (SEQ ID No.1) and the parent (wild-type (wt)) sequence (SEQ ID No. 3). In FIG. 1, the humanized protective antigen (HoPA) (upper sequence) SEQ ID No. 1 is the human optimized gene and PA (lower sequence) is the parent wild-type gene. Asterisks denote nucleotides that align. FIG. 1 A-C shows alignment of by 1-780; 781-1560; and 1561-2208, respectively.

DETAILED DESCRIPTION OF PREFERRED EMBODIMENTS

Figure 2:
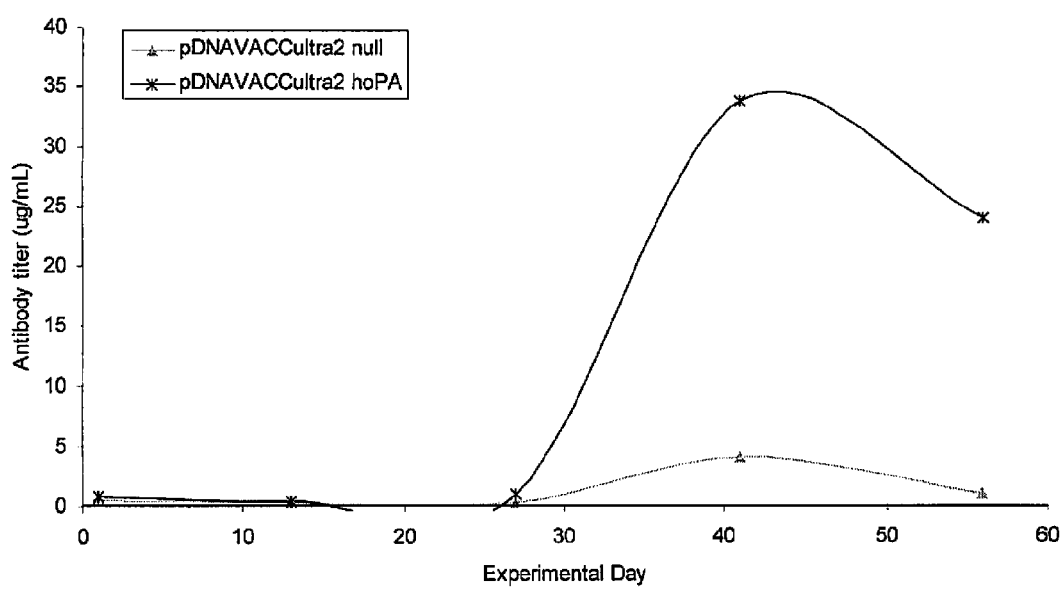
FIG. 2. Evaluation of DNA vaccines. During this 56 day study A/J mice (n=8 per group) injected IM with pDNAVAC-Cultura2™-HoPA encoding the human optimized PA gene with the tissue plasminogen activator (TPA) signal sequence elicited a robust anti-PA IgG response during the 14 days following the second boost. This response gradually contracted over the final 14 days of the study.
Figure 3:
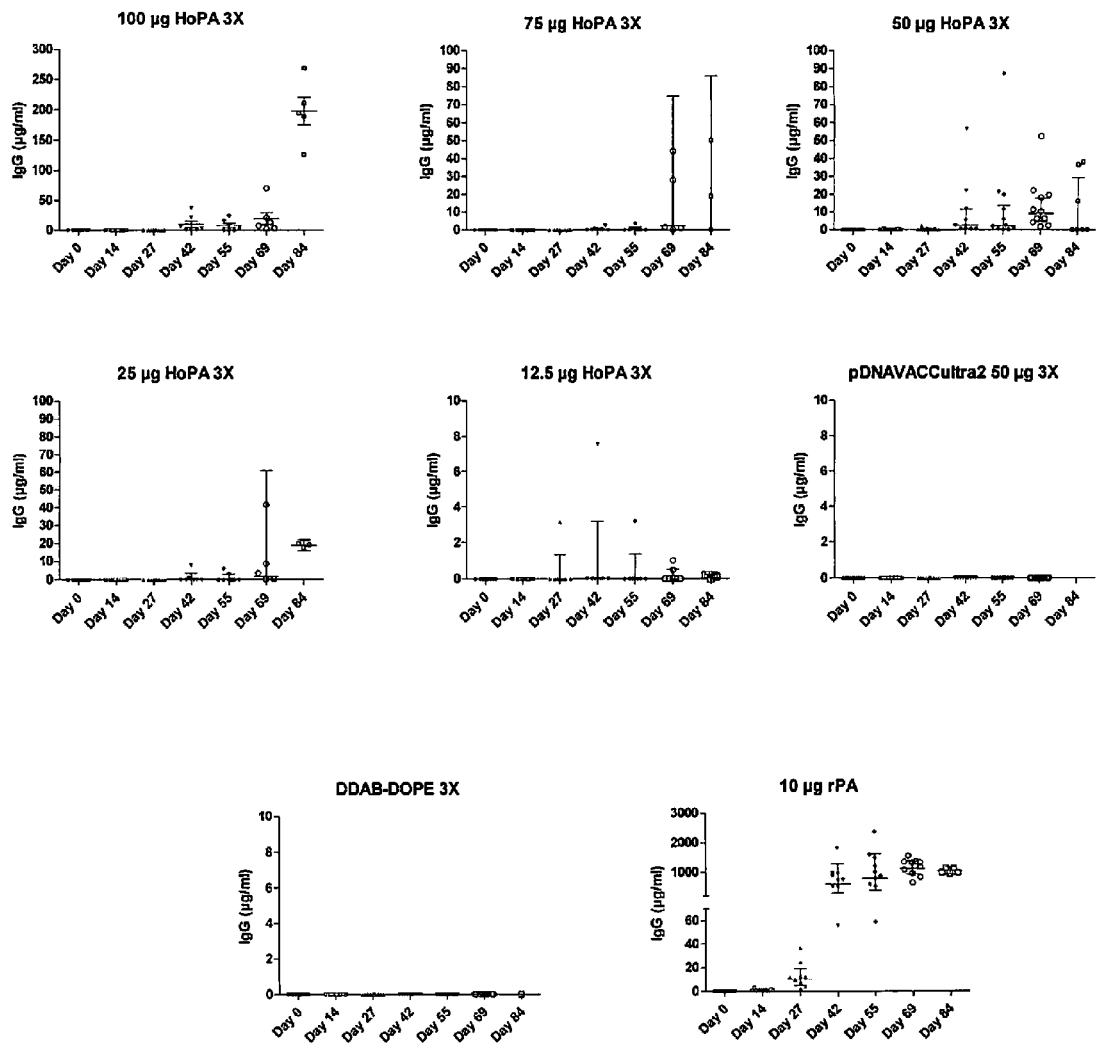
FIG. 3. Anti-PA IgG titers in response to homologous prime-boost-boost with pDNAVACCultra2™-HoPA. Eight groups of mice (n=10) were immunized IM with pDNAVAC-Cultra2™-HoPA on three separate occasions 28 days apart. Control groups were injected with pDNAVACCultra2 without HoPA, the lipid adjuvant dioleoyl phosphatidylethanolamine-dimethyl dioactadecylammoniium bromide (DDAB-DOPE) only, and 10 µg of rPA injected with Alum adjuvant. Titers were low in comparison to the control rPA treated group.
Figure 4:
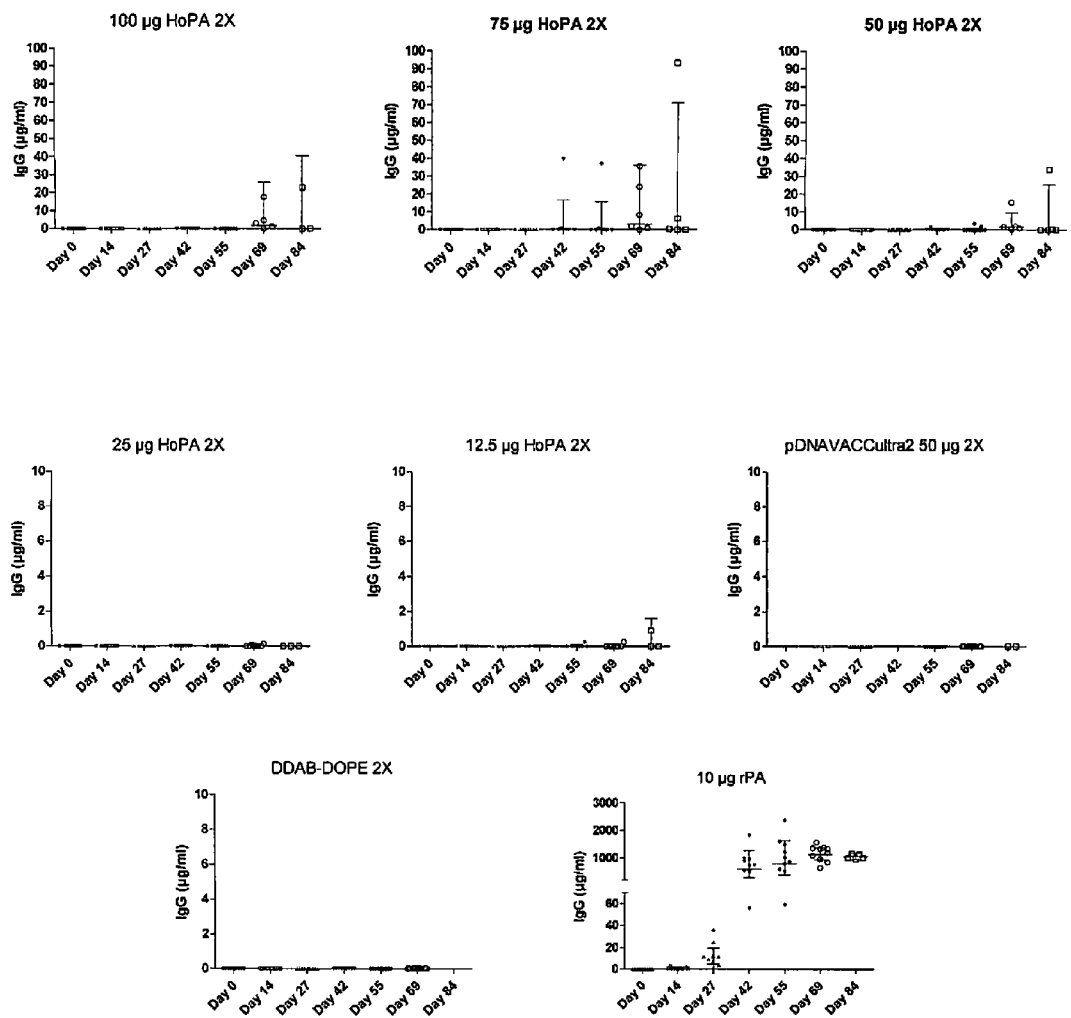
FIG. 4. Anti-PA IgG titers in response to homologous prime-boost with pDNAVACCultra2™-HoPA. Eight groups of mice (n=10) were immunized IM with pDNAVACCultra2™-HoPA on two separate occasions 28 days apart. Control groups were injected with pDNAVACCultra2 without HoPA, the lipid adjuvant (DDAB-DOPE) only, and 10 µg of rPA injected with Alum.
Figure 5:
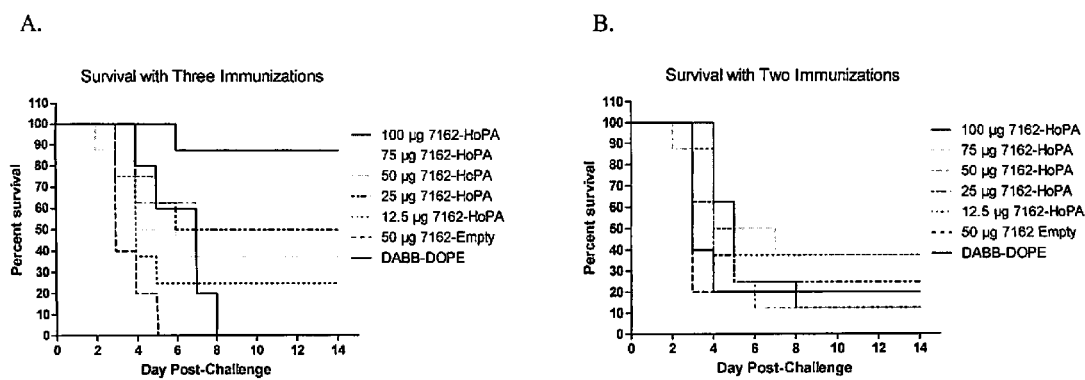
FIG. 5. Efficacy of a homologous prime-boost-boost and a prime-boost with pDNAVACCultra2™-HoPA. Eight groups of mice (n=10) were immunized IM with pDNAVACCultra2™-HoPA two separate occasions 28 days apart. Fourteen days after the last immunization all mice were challenged with $LD_{50}$s of *B. anthracis* Sterne strain spores. Survival was significantly improved at 90% with three 100 μg doses of pDNAVACCultra2-HoPA, designated in the figure legend as 7162-HoPA, relative to the lower less frequent doses. Recombinant PA protected 100% of the mice.
Figure 6:
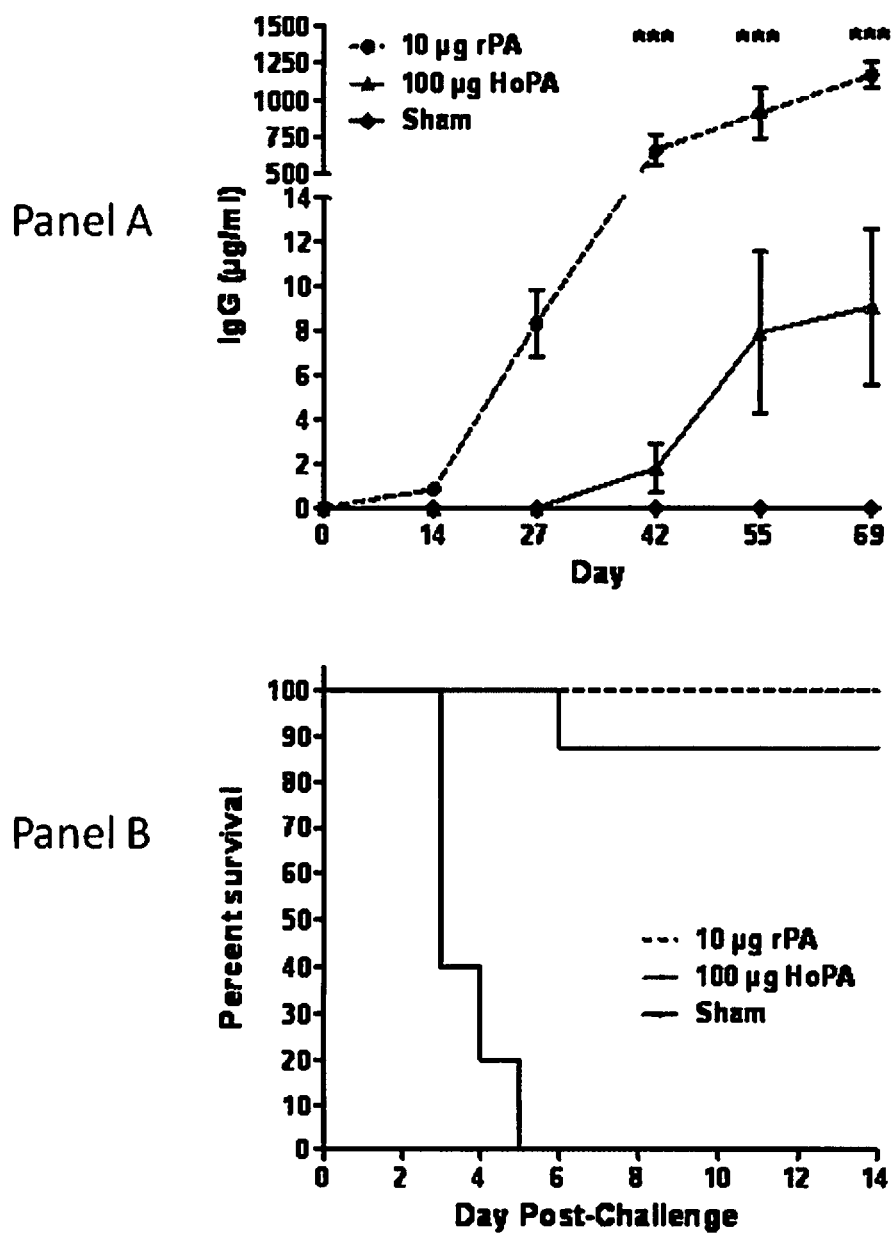
FIG. 6. Anti-PA IgG titers and survival in response to homologous prime-boost-boost with humanized protective antigen.

The following terms are defined:
An immunogenic composition is a composition, containing one or more antigens, including proteins or peptides or nucleic acid expression systems that express immunogenic proteins or peptides in vivo for the induction of a humoral or cell mediated immune response; a vaccine is an immunogenic composition used to induce protective immunity; a DNA expression system is a molecular system containing plasmid or closed loop DNA containing elements for expressing an inserted DNA sequence as polypeptide; a viral expression system is any viral based system, including viral like particles or viral replicons, containing elements for expressing an inserted DNA sequence as a polypeptide.

Immunization of susceptible individuals through the process of vaccination has long been the most desirable approach to disease prevention. This is particularly important in anthrax since manifestation of the disease results in high mortality. Therefore, it is preferred to prophylactically protect against infection rather than attempt to administer antibiotic post-infection.

The current licensed vaccine in the U.S. for anthrax is a cellular filtrate of *B. anthracis* that mostly contains PA (Baillie, L., J Appl Microbiol, 91: 609-613 (2001)). Unfortunately, due to the nature of the vaccine, batch to batch variability occurs, resulting in inconsistency in efficacy.

In order to alleviate these problems, recombinant technology has been employed. Nucleic acid based, or DNA vaccines represent a relatively recent and attractive vaccination modality. This interest has been stemmed by their inexpensive and easy production, high stability, and flexibility regarding cloning and delivery method. The basic structure of a DNA vaccine is a plasmid or closed loop of DNA (the plasmid "backbone") that contains a selectable marker, a mammalian promoter such as the CMV promoter for tissue specific expression, and the gene encoding the antigen of interest, in this case protective antigen (PA).

In principal, the DNA is delivered to either immunologically relevant cells of the skin or to cells that have highly active transcription and translation machinery such as muscle cells where the PA gene is expressed via the CMV promoter, released and displayed from the cell, and hopefully picked up by a scavenging dendritic cell or macrophage.

Unfortunately, DNA vaccines in primates and humans often do not elicit humoral or antibody based responses (Calarota, et al., Lancet, 351: 1320-1325; Coban, et al., Infect Immun., 72: 584-588 (2004); Epstein, et al., Hum Gene Ther, 13: 1551-1560 (2002); Klinman, et al., Curr Top Microbiol Immunol, 247: 131-142 (2000); Wang, et al., Science, 282: 476-480 (1998)) which are critical to surviving an anthrax infection. Several approaches have been developed to enhance the immunogenicity of DNA vaccines including the use of adjuvants, altering the delivery system, modifying the plasmid backbone by including CpG motifs, or altering the codon bias (Leitner, et al., Vaccine, 18: 765-777 (1999); O'Hagan, et al., Nat Rev Drug Discov, 2: 727-735 (2003)).

The current invention relates to a DNA construct, useful in vaccine formulations, utilizing a novel human codon-optimized PA gene sequence. The current invention, unlike previously described methods of DNA optimization, not only permits efficient expression of recombinant protein, but also enables expression of protein tertiary structure, with fidelity to the native bacterially expressed protein. PA expression from *B. anthracis* is optimized through consideration of a number of factors that enable efficient expression in a mammalian host, e.g., human. The factors considered in the process also improve the likelihood of greater tertiary structural similarity between the expressed recombinant protein and native, bacterially expressed PA. The result is a greater likelihood of a more efficacious induction of adaptive immunity.

Method for Humanizing DNA Sequence

DNA vaccines rely heavily on the natural processes of transcription and translation by the eukaryotic host cell. Bacterial gene structures are very different from the human host and require specialized transcriptional and translational apparatuses. These differences include a lack of introns (noncoding regions that eukaryotes splice out of message RNA), the presence of operons (multiple genes in one message), and a variety of secondary structures within the mRNA that are foreign in eukaryotes (Strugnell, et al., Immunol Cell Bio, 75: 364-369 (1997)). Additionally, bacterial proteins are not glycosylated by the bacterial system but contain amino acid motifs which are efficiently and inappropriately glycosylated by eukaryotic cells. Bacterial mRNA also lacks appropriate structures and sequences to insure an effective half-life in eukaryotic cells.

A important additional difference between eukaryotic and prokaryotic transcriptional/translational systems is the significant differences in codon usage and the arrangement of nucleotides in bacterial mRNA that give rise to codons that are rare in eukaryotic mRNA (Manoj, et al., Crit Rev Clin Lab Sci, 41: 1-39 (2004)). These differences may be explained by the composition of the tRNA pool that is available to the host for translation or the guanine/cytosine (GC) and adenine/thymidine (AT) percentages of the bacterial gene and their similarity to the eukaryotic host (Saler, Nat Rev Drug Discov, 2: 727-735 2003)). Coincident with these differences is the operation of the ribosome and the complex combinations of RNAs and proteins that comprise the translational machinery.

During translation, the ribosome attaches to the mRNA by a specific recognition operation. As the ribosome proceeds down the mRNA it specific codons are recognized leading to a defined assembly of amino acids to ultimately build the nascent protein. Ribosomes have been shown to complete this protein synthesis in a complex manner moving down the mRNA at a varying rate of progression resulting in a multitude of different structural results. If a ribosome slows in its progression, it disconnects from the RNA resulting in premature termination of translation.

Variations in the rate of ribosomal processivity can result in the creation of important structural features. For example, pausing is thought to allow proteins to create protein folds, allowing complex intra-molecular associations to occur. These associations can give rise to proper protein function but also create important immunogenic motifs, that are not present from the linear sequence.

However, when bacterial sequences are expressed from eukaryotic host systems, variations, away from that seen in the bacteria, can result in significant differences in ribosomal procession, glycosylation and even premature termination of translation. The result, therefore, in developing immunogenic compositions, are proteins that may not mimic native protein immune induction.

In developing a more antigenically efficient PA protein, genetic incompatibilities between bacterial and eukaryotic genomes were mitigated by modifying the bacterial sequence in order to conform to optimal codon usage in eukaryotic hosts.

There are many approaches that can be taken in the effort to produce bacterial gene sequences that are translated in human cells more efficiently. The most common is to synthesize the new gene sequence using only the most highly used codon in the host organism. However, this method does not take into account differences between prokaryotic and eukaryotic transcription and translational machinery or the guanine/cytosine (GC) and adenine/thymidine (AT) content of the bacterial gene.

The approach utilized in the current invention is to modify the bacterial gene in order to permit expression resulting in a greater likelihood of maintaining fidelity to the bacterially expressed native protein. This is termed here as "human optimization." The aim of this approach is to produce a recombinant protein with a greater likelihood of inducing a more efficacious adaptive immune response.

In the inventive method to modify proteins for efficient expression of antigens in a eukaryotic host a number of factors are taken into account. These are summarized as:
  a. efficiency of translation;
  b. fidelity of protein folding;
  c. minimize excision of mRNA regions by recognition by the post-transcriptional machinery of mammalian host cell;
  d. avoidance of single-stranded RNA folding due to resultant mRNA sequence complementarity.

In the inventive method, the early (i.e., first region) of the gene utilizes codons most highly utilized by the mammalian host cell. This consideration, therefore, improves the efficiency of gene expression by minimizing the likelihood of early termination of the ribosome. Although the extent of the sequence that is left unaltered varies from gene to gene, the region is typically up to 100 bp.

An important consideration is the fidelity of the tertiary structure and folding of the protein produced in eukaryotic cells to the native, bacterially expressed protein. It is recognized that important immunogenic epitopes are likely to exist beyond the linear or even secondary peptide structure. Rather, proper protein folding can bring amino acids or even peptide sequences, that are normally considerably downstream of each other, into juxtaposition, creating important immunogenic conformational epitopes.

To improve the likelihood of producing these epitopes in the recombinant protein, a search of the native PA sequence is undertake in order to ascertain and identify regions containing relatively heavy concentrations of rare codons. These regions may represent domains with specific folding motifs within the normal, native PA protein. Therefore, retention of these regions in the modified sequence is incumbent upon substituting the rare bacterial codons with complimentary rare codons from the human bias table. This would permit ribosome progression to slow, where it normally would in the bacteria, and permit normal folding to occur.

In order to ensure against unwarranted deletions of mRNA the bacterial sequence is analyzed with the aim of identifying ribosomal splice sites. Alteration of these regions, therefore, will ensure that post-transcriptional machinery of mammalian cells does not inadvertently delete sections of the mRNA Finally, an analysis of the bacterial sequence is undertaken to identify any regions of complementarity. These regions are of importance since these regions could potentially result in single stranded RNA folding back on itself, resulting in unwanted host cell operations, such as ribosomal stalling or premature termination of translation.

Collectively, the inventive method avoids "over optimization" of the bacterial gene sequence. Instead, the method provides a more deliberate procedure leading to an expressed protein with greater antigenic similarity to native, bacterially expressed protein.

EXAMPLE

Design of Humanized *Bacillus anthracis* Protective Antigen (PA)

In order to illustrate the inventive method, the human optimization of PA (HoPA) was undertaken. As discussed above, the factors that were considered in the development of the humanized gene sequence. The features of HoPA include:
  a. highly used codons for the first 50 codons of the sequence, thereby effectively engaging the ribosome and reducing premature termination;
  b. using rare codons from the human codon bias table in the same positions where the wildtype PA gene sequence used rare codons from the *Bacillus anthracis* codon usage table thus insuring that where the bacterial ribosome paused during protein synthesis in the bacteria, the mammalian ribosome did as well;
  c. ensuring that regions, where there are many rare codons close together, are maintained but the actual number of rare codons reduced in order to minimize the likelihood of ribosomal progression slowing or stalling;
  d. a search for cryptic ribosomal splice sites was undertaken to ensure that the post-transcriptional machinery of the mammalian cells did not delete sections of the mRNA;
  e. secondary structure determinations to ensure that the resulting mRNA did not have long regions of complementarity that would result in a single stranded RNA that was folded back onto itself, into a secondary structure that could not be resolved by the ribosome also leading to premature termination of the translation process.

Human optimization was performed on the non-proprietary wild-type PA gene (GenBank Accession no. AAA22637.1). In designing the new sequence, the factors, above, were considered and incorporated into the new human optimized sequence (HoPA). The new HoPA gene sequence is illustrated in FIG. 1 (A-C) adjacent to the native sequence. The optimized sequence is also listed in SEQ ID No. 1.

Unlike in the native sequence, the new nucleotide sequence lacks many of the rare codons and motifs that hinder expression in eukaryotes while using human rare codons to emulate the overall spacing of rare codons. An important consideration is to avoid over optimization of the gene sequence. Over optimization may result in the most common eukaryotic codons depleting the available reservoir of normally abundant tRNAs. This process may artificially accelerate the processivity of the ribosome, increasing the chance that the nascent protein will not fold into the proper secondary structure.

The newly synthesized PA gene also included Sap1 restriction sites at the N- and C-terminal ends to allow effective cloning into the multi-cloning site of the pDNAVACCultra2™ (Nature Technology, Lincoln, Nebr.) construct. At the same time, the amino terminal *Bacillus* leader peptide was eliminated since cloning into pDNAVACCultra2™ places the human TPA leader peptide upstream and in-frame of the PA sequence. This modification effectively increases extracellular trafficking of the recombinant PA (rPA) protein by eukaryotic cells. Ultimately, due to codon redundancy, when both genes are translated they result in the same wild-type amino acid sequence, as illustrated in SEQ ID No. 1.

In order to evaluate the expression of HoPA in a eukaryotic cell line Chinese hamster ovary (CHO) cells strain K1 was transfected with pDNAVACCultra2™-HoPA and pDNAVACCultra2™-HoPA carrying the green fluorescent protein (GFP). Efficient transfection and the transcription/translation of HoPA were verified by the expression of GFP from the modified HoPA-GFP vector. Western blot analysis of supernatants from the transfected CHO-K1 cells after 20 hr demonstrated the presence of PA. This study confirmed that HoPA with it's codon optimizations, could be expressed from a eukaryotic cell line using the host cell machinery.

Referring to FIG. 2, analysis of the mouse antibody response following immunizations with HoPA cloned into NTC's pDNAVACCultra2™ DNA vaccine expression vector demonstrated that the animals had mounted PA specific IgG responses. The efficacy of the human TPA sequence at the beginning of HoPA, to direct the synthesized PA protein out of the cell for detection and processing by circulating immune cells, was evaluated.

In the first study 50 μg pDNAVACCultra2™-HoPA or pDNAVACCultra2™-null (no insert) were mixed with a lipid adjuvant prior to being intramuscularly injected into mice (n=8) on three separate occasions 28 days apart. Serum anti-PA IgG titers were tracked for 56 days and demonstrated that following the second homologous boost on day 28 the rPA specific IgG titer increased from baseline to 33.8 μg/ml (FIG. 2).

In another animal study the efficacy following multiple administrations was evaluated (FIG. 3). In this study efficacy was evaluated after injecting various doses (100, 75, 50, 25, and 12.5 μg) of pDNAVACCultra2™-HoPA once, twice, and three times. Serum IgG titers were tracked as before. Dose and frequency related responses were observed, with the highest antigen specific titers (FIG. 3) achieved with the highest dose of DNA injected three times. The same doses of vaccine given twice (days 28 and 42) (FIG. 4) or once did not generate as robust an IgG response as the triple vaccination schedule or rPA.

Two weeks after the last vaccination the mice were challenged intraperitoneally with 40 $LD_{50}$s of *B. anthracis* Sterne strain spores ($4.03\times10^5$ CFU/mouse). Survival was tracked over the course of 14 days (FIG. 5). Survival was significantly improved ($p<0.05$) with 100 μg of pDNAVACCultra2™-HoPA (designated as 7162-HoPA in the figure below) when administered three times. Doses less than 100 μg or immunization schedules that lacked a second booster are not efficacious. In comparison, 10 μg of rPA protected 100% of the challenged mice. These results speak to the efficacy of HoPA when cloned into the pDNAVACCultra construct. In FIG. 5, the negative control is the use of the adjuvant Dioleoyl phosphatidylethanolamine-dimethyl dioctadecylammonium bromide (DDAB-DOPE).

FIG. 6 illustrates the immunoglobulin concentration following immunization with humanized PA. As seen in panel A, a significant humoral response is evident following either recombinant PA protein or HoPA. However, significantly less antibody response is seen following immunization with the DNA expressed HoPA than following immunization with rPA protein. The clear dichotomy of immunoglobulin induction seen in FIG. 5 between HoPA (expressed from an administered DNA vector) and rPA protein administration induced between is likely dependent on the expression efficiency of the DNA expression system.

Additionally, antibody induced by HoPA was capable of efficiently neutralizing lethal toxin, as evidenced by toxin neutralization activity (TNA) assay. These results are summarized in Table 1. The assay was conducted as described by Quinn, C. P., et al., J. Infect. Dis. 190: 1228-1236 (2004). Prior to testing, recombinant PA (rPA) and recombinant LF (rLF) were titrated for toxin potency with J774A.1 cells. The concentrations of rPA and rLF that resulted in more than 99% cell lysis at a fixed cell density of $2\times10^4$ cells/well were 45.1 and 36.1 ng/ml, respectively. Serum samples were serially diluted starting at 1:50 out to 1:102400 and were assayed in quadruplicate. The resulting serum neutralization curve (antibody dilution factor versus optical density was analyzed with a four-parameter logistic log fit curve. The primary endpoint calculated from this 4-PL curve is the 50% effective antibody dilution ($ED_{50}$) that protects 50% of the eukaryotic cells in the assay. This value is reported as the reciprocal of the antibody dilution corresponding to the inflection point ("c" parameter) of the four-parameter logistic log fit of the serum neutralization curve. An $ED_{50}$ greater than 200 is correlated with survival (Pitt, M. L., et al., Vaccine 19: 4768-4773 (2001). Vaccination with pDNAVACCulture2-HoPA three times elicited antibody responses by day 69 (FIG. 6A) with sufficiently high toxin neutralization capacities greater than 200 $ED_{50}$.

TABLE 1

| Mouse | $ED_{50}$ |
|---|---|
| 1.3 | 587.8 |
| 1.4 | 409.4 |
| 1.7 | 1144.7 |
| 1.8 | 272.2 |

A further demonstration of the effectiveness of the humoral response induced by HoPA is illustrated in FIG. 6B. In FIG. 6B, mice were immunized with either rPA protein or plasmid-HoPA expression plasmid (pDNAVACCultra™). In FIG. 6B, the survival of mice following anthrax challenge, that had been immunized with HoPA, was equivalent to that observed for the recombinant protein, despite the much higher levels of immunoglobulin induced. The improved efficacy of the immunoglobulin over that induced from rPA protein likely represents the greater similarity of HoPA to native PA structure. Additionally, HoPA may induce higher affinity anti-PA antibody or higher concentrations of antibody specific to regions on the native PA molecule that are more relevant to immune protection. One explanation is that HoPA may induce helper T-cell response to induce IL4. This may suppress IgG2a and IgG2b responses and increase IgG1.

Although the example shown expressed the novel PA in the pDNAVACCultra™ construct, expression of the optimized PA construct can be inserted and expressed by other suitable expression systems. This could include other DNA and viral expression systems.

What is claimed is:

1. A method of modifying a recombinant bacterial gene for expression in a mammalian host comprising:
   a. replacing highly utilized host codons in the first 2 to 5 percent of the total bacterial gene sequence;
   b. replacing regions of the sequence where there are stretches of three or more rare bacterial codons with rare mammalian host codons.
   c. identifying regions of complementarity, wherein the regions of complementarity could result in RNA folding back on itself and removing said regions of complementary by altering the codons, while retaining the expressed amino acid at that position in the protein.

2. The method of claim 1, wherein said mammalian host is human.

3. The method of claim 1, wherein the bacterial gene is recombinant *Bacillus anthracis* protective antigen.

4. The method of claim 1, wherein cryptic ribosomal splice sites are deleted by altering the codons in that region while retaining the expressed amino acid at that position in the protein.

5. The method of claim 3, wherein the first 50 codons of said recombinant *Bacillus anthracis* protective antigen are highly utilized human codons.

* * * * *

SEQUENCE LISTING

<160> NUMBER OF SEQ ID NOS: 3

<210> SEQ ID NO 1
<211> LENGTH: 2208
<212> TYPE: DNA
<213> ORGANISM: Bacillus anthracis

<400> SEQUENCE: 1

| | | | | | | |
|---|---|---|---|---|---|---|
| gaagtgaagc | aggagaatcg | gctgctgaat | gaatccgaga | gcagctctca | gggcttgctg | 60 |
| gggtattact | tctctgacct | gaatttccag | gcacccatgg | tcgtcacatc | ctctaccacc | 120 |
| ggagacctat | cgattccctc | aagcgagctg | gagaatatcc | cttcagagaa | ccagtatttt | 180 |
| caatccgcaa | tctggtccgg | cttcattaaa | gtgaagaagt | ctgatgaata | caccttcgcc | 240 |
| acttccgcag | acaatcacgt | taccatgtgg | gtggacgacc | aagaagtcat | taataaagcc | 300 |
| tctaattcca | ataaaatcag | actcgaaaag | ggcagacttt | atcagatcaa | gattcagtac | 360 |
| cagagggaga | atcccacaga | aaaggtttg | gatttcaaat | tgtattggac | agatagtcag | 420 |
| aataagaaag | aggtgatatc | ctctgacaac | ctccagctgc | ccgaattgaa | acaaaaatca | 480 |
| tcaaattcac | ggaagaagcg | ctctacctca | gccggcccaa | ccgtccctga | cagagataac | 540 |
| gacgggattc | cagattctct | ggaggttgag | ggctacacag | tggacgtaaa | gaacaagaga | 600 |
| acctttttga | gtccttggat | ttcaaacatt | catgagaaga | agggacttac | taagtacaag | 660 |
| tctagcccag | agaaatggag | cacagcctcc | gatccatact | cggacttcga | gaaggtcacc | 720 |
| ggacgcatcg | ataagaatgt | aagcccagag | gctcggcatc | cactggtggc | tgcctatccc | 780 |
| attgtgcacg | tggatatgga | aaatattatt | ctcagcaaga | acgaggatca | gtccactcaa | 840 |
| aacacggact | ccgagacaag | aaccatcagc | aagaacacat | ctacaagtag | aactcataca | 900 |
| tcagaggtgc | acggcaacgc | cgaggttcac | gccagtttct | tcgatatcgg | gggcagtgtt | 960 |
| agcgccggat | tttctaactc | caacagctct | acagtggcta | tcgaccactc | tctgagtctc | 1020 |
| gcaggggagc | ggacgtgggc | ggaaaccatg | ggcctgaaca | ccgccgatac | agccaggttg | 1080 |
| aatgcaaaca | ttcgctatgt | gaatacaggt | accgctccca | tctataatgt | ccttcctact | 1140 |
| acatctctcg | tgttggggaa | aaatcagacc | ctggcaacaa | tcaaggccaa | ggagaatcag | 1200 |
| ctgagtcaga | tactcgcacc | caataactac | tacccatcaa | agaatcttgc | acctatagct | 1260 |
| ctgaacgccc | aggatgattt | tagcagcacc | ccaattacta | tgaattataa | ccagttcctg | 1320 |
| gagttggaga | agactaagca | attgaggctg | gatacagacc | aagtgtacgg | caatatagct | 1380 |
| acttataact | tcgagaatgg | gagggttagg | gtggacacag | ggagcaattg | gtcggaagtg | 1440 |
| cttccacaaa | ttcaggagac | cacagccaga | atcatcttta | atggcaagga | cctcaacctt | 1500 |
| gtggaaagga | gaattgccgc | agttaaccca | agtgaccct | tggaaacaac | caagccagac | 1560 |
| atgactctga | aggaagccct | gaagatcgct | ttcgggttta | atgaaccaaa | cggcaacctg | 1620 |
| cagtaccagg | gaaaggacat | taccgagttt | gactttaatt | tcgatcagca | gacctcccaa | 1680 |
| aacatcaaga | atcaactggc | cgagctgaac | gctacaaata | tttataccgt | gctcgacaag | 1740 |
| attaaattga | acgcgaagat | gaatatcttg | atacgcgata | agcgctttca | ttacgaccgc | 1800 |
| aacaatatag | ccgttggcgc | cgacgaatct | gtcgtaaaag | aggcccacag | agaagtgatt | 1860 |
| aactccagca | ccgaagggct | cctgctgaac | attgataaag | acatccgcaa | gatcctgtcc | 1920 |
| gggtacatag | tggagatcga | ggacaccgag | ggactcaaag | aagtaatcaa | cgaccggtac | 1980 |
| gatatgctga | atatctcaag | cctccggcaa | gacgggaaga | cttcatagat | ttcaagaaa | 2040 |
| tacaacgaca | agctgccact | ctatatctca | aaccccaatt | acaaggtgaa | cgtttacgca | 2100 |

```
     gtcaccaaag agaacaccat cattaatcca tcagaaaatg gtgacacaag tactaatggt   2160
attaagaaga ttctcatttt cagcaagaag gggtatgaga tcggctaa               2208
```

<210> SEQ ID NO 2
<211> LENGTH: 735
<212> TYPE: PRT
<213> ORGANISM: Bacillus anthracis

<400> SEQUENCE: 2

```
Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350
```

```
Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 3
<211> LENGTH: 1680
<212> TYPE: DNA
<213> ORGANISM: Bacillus anthracis

<400> SEQUENCE: 3

-continued

```
gaagttaaac aggagaaccg gttattaaat gaatcagaat caagttccca ggggtggata      60
ctattttagt gatttgaatt ttcaagcacc catggtggtt acctcttcta ctacagggga     120
tttatctatt cctagttctg agttagacaa tctgctattt ggtcaggatt tatcaaagtt    180
aagaagagtg atgaatatac atttgctact tccgctgata atcatgtaac aatgtgggta    240
tctaattcta acaaaatcag attagaaaaa ggaagattat atcaaataaa aattcaatat    300
caacgagaaa atcctactga aaaggattgg gatttcaaga ataaaaaaga agtgatttct    360
agtgataact tacaattgcc agaatcgaac tcaagaaaaa agcgaagtac aagtgctgga    420
cctacggttc gatggaatcc ctgattcatt agaggtagaa ggatatacgg ttgatgtcaa    480
acttttcttt caccatggat ttctaatatt catgaaaaga aaggattaac caaatataaa    540
tcatctcctg aaaaatggag cacggcttct gatccgggac ggattgataa gaatgtatca    600
ccagaggcaa gacaccccct tattgtacat gtagatatgg agaatattat tctctcaaaa    660
aatgaggaat actgatagtg aaacgagaac aataagtaaa aatacttcta caagtaggac    720
agtgaagtac atggaaatgc agaagtgcat gcgtcgttct ttgatatttc tgcaggattt    780
agtaattcga attcaagtac ggtcgcaatt gatgcagggg aaagaacttg ggctgaaaca    840
atgggtttaa ataccgctga atgccaatat tagatatgta aatactggga cggctccaat    900
ctacaacttc gttagtgtta ggaaaaaatc aaacactcgc gacaattaaa gctaaggaaa    960
accaattaag tcaaatactt gcacctaata attattatcc ttctattaaa tgcacaagac   1020
gatttcagtt ctactccaat tacaatgaat gagttagaaa aaacgaaaca attaagatta   1080
gatacggatc aagtatacat acaattttga aaatggaaga gtgagggtgg atacaggctc   1140
gttaccgcaa attcaagaaa caactgcacg tatcattttt aatggaaaag atttaagtag   1200
aaaggcggat agcggcggtt aatcctagtg atccattaga aacgactaaa ccggatatga   1260
cattaaaaga agcccttaaa atagcatttg gatttaacga accgaatgga aacttacaat   1320
atcaagggaa agacataacc gaatttgatt ttaatttcga tcaacaaaca tctcaaatct   1380
gaactggagt gaagtgatgg gaatatagca tacaatcaat ttcttaaaac ttggcgccaa   1440
tcgcaacgtg ttaccaacga tacagcaaga ttacattcac tatctctagg tgggagtgta   1500
acatactatc aatccacaca ggtggcagct tatccgtaca gtgatttcga aaaggttaca   1560
aaataaaaga cagaccgtga caatttaaaa caaaaatctt tgtactggac cgattctcaa   1620
gatgaccaag aagtgattaa taaagctaaa tattccatcg gaaaaccaat atttttacta   1680
```